United States Patent
Sebti et al.

(10) Patent No.: US 10,507,228 B2
(45) Date of Patent: Dec. 17, 2019

(54) METHODS AND COMPOSITIONS RELATED TO KRAS INHIBITORS

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Said M. Sebti, Tampa, FL (US); Jianfeng Cai, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 15/567,655

(22) PCT Filed: Apr. 20, 2016

(86) PCT No.: PCT/US2016/028405
§ 371 (c)(1),
(2) Date: Oct. 19, 2017

(87) PCT Pub. No.: WO2016/172187
PCT Pub. Date: Oct. 27, 2016

(65) Prior Publication Data
US 2018/0185439 A1    Jul. 5, 2018

Related U.S. Application Data

(60) Provisional application No. 62/149,904, filed on Apr. 20, 2015.

(51) Int. Cl.
| | |
|---|---|
| *A61K 38/12* | (2006.01) |
| *A61K 38/10* | (2006.01) |
| *A61K 38/00* | (2006.01) |
| *C07K 7/56* | (2006.01) |
| *C07K 7/08* | (2006.01) |
| *C07K 7/50* | (2006.01) |
| *C07K 14/82* | (2006.01) |
| *C07K 14/47* | (2006.01) |

(52) U.S. Cl.
CPC .............. *A61K 38/12* (2013.01); *C07K 7/56* (2013.01); *C07K 14/4703* (2013.01); *C07K 14/82* (2013.01); *A61K 38/00* (2013.01)

(58) Field of Classification Search
CPC ........ A61K 38/12; A61K 38/10; A61K 38/00; C07K 7/56; C07K 7/08; C07K 7/50; C07K 14/4703; C07K 14/82
USPC ........ 514/21.1, 21.5, 1.1; 530/326, 317, 300
See application file for complete search history.

(56) References Cited

U.S. PATENT DOCUMENTS

| | | | |
|---|---|---|---|
| 4,559,157 | A | 12/1985 | Smith et al. |
| 4,608,392 | A | 8/1986 | Jacquet et al. |
| 4,820,508 | A | 4/1989 | Wortzman |
| 4,992,478 | A | 2/1991 | Geria |
| 2006/0263294 | A1 | 11/2006 | Bergman et al. |
| 2006/0275213 | A1 | 12/2006 | Bergman et al. |
| 2012/0270800 | A1 | 10/2012 | Verdine et al. |
| 2014/0018302 | A1 | 1/2014 | Walensky et al. |
| 2015/0266939 | A1* | 9/2015 | Vogan ............... C07K 14/50 424/135.1 |

FOREIGN PATENT DOCUMENTS

| | | | | |
|---|---|---|---|---|
| WO | WO-03025205 | A2 * | 3/2003 | ......... G01N 33/6872 |
| WO | WO-2013138795 | A1 * | 9/2013 | ............. C07K 14/50 |

OTHER PUBLICATIONS

International Search Report & Written Opinion issued in corresponding application No. PCT/US2016/028405 dated Jul. 26, 2016, 6 pgs.

* cited by examiner

*Primary Examiner* — Julie Ha
(74) *Attorney, Agent, or Firm* — Meunier Carlin & Curfman LLC (57) ABSTRACT

Stapled peptides and methods of using them to inhibit the Kras/Raf interaction are disclosed herein.

8 Claims, 2 Drawing Sheets

Specification includes a Sequence Listing.

FIG. 1A

FIG. 1B

METHODS AND COMPOSITIONS RELATED TO KRAS INHIBITORS

CROSS-REFERENCE TO RELATED APPLICATIONS

This application is a national stage application filed under 35 U.S.C. § 371 of PCT Application No. PCT/US2016/028405, filed Apr. 20, 2016, which claims the benefit of U.S. Provisional Application No. 62/149,904, filed Apr. 20, 2015, which is hereby incorporated herein by reference in its entirety.

BACKGROUND

Kras is one of ras genes that undergo mutation in various cancers. Mutations are frequently limited to only one of the ras genes, and the frequency is tissue- and tumor type-specific. Ras-binding domains/Ras-associating domains (RBD/RAD) are the primary Ras-binding sites in Ras effector proteins. Raf-1 is a pivotal effector of Ras. Among the Ras family members, it is preferentially activated by KRAS, showing that its RBD predominantly interacts with KRAS.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to specific inhibitors of the Kras/Raf interaction, and their use in the treatment of disease.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

As used herein, the term "composition" is intended to encompass a product comprising the specified ingredients in the specified amounts, as well as any product which results, directly or indirectly, from combination of the specified ingredients in the specified amounts.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a patient can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Compositions

Figure 1A:
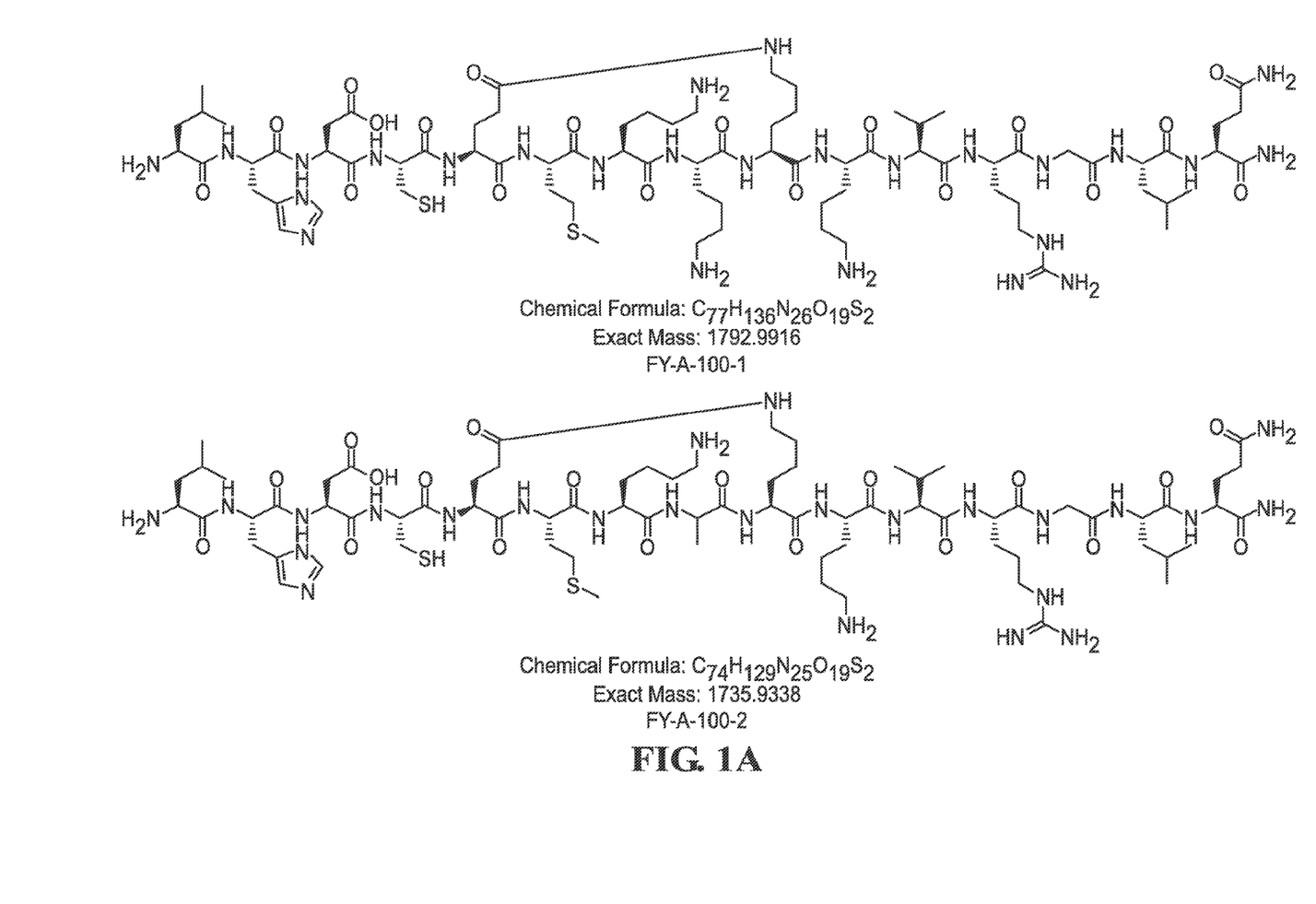
FIGS. 1A and 1B illustrate that stapled peptides designed based on the helical domain (78-92, LHDCLMKALKVRGLQ) (SEQ ID NO: 1) of Raf RBD inhibit mt Kras binding to GST-RBD.
Figure 1B:
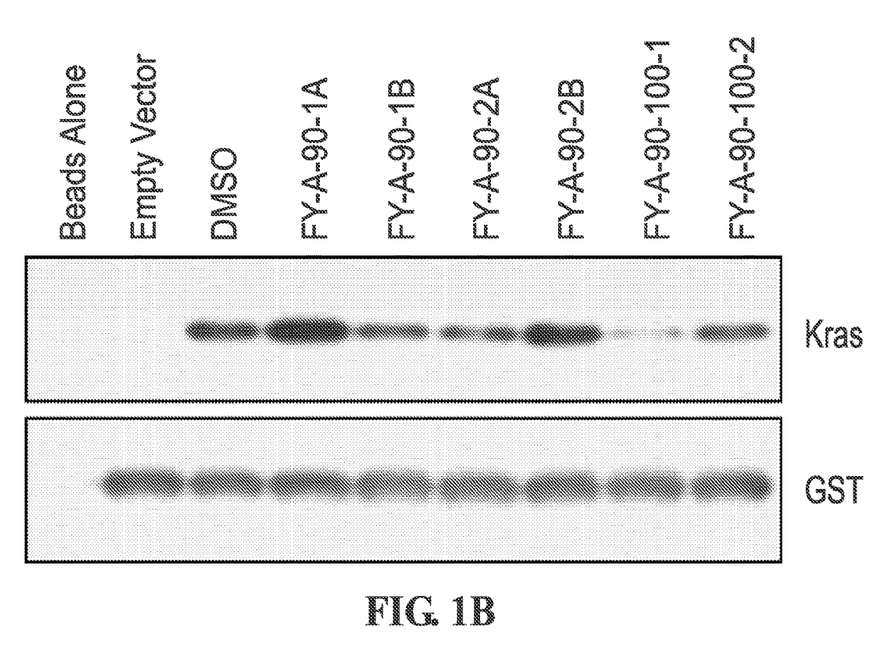

Several stapled peptides such as FY-A-100-1 and 2 have been made (see FIG. 1A) that were designed based on the helical domain (78-92, LHDCLMKALKVRGLQ) (SEQ ID NO. 1) of Raf RBD (Ras binding domain). The synthesis was conducted on solid phase. In GST-RBD pulldown assays, FY-A-100-1 was potent at inhibiting the ability of GST-RBD to bind mt G12D KRas from lysates of NIH-3T3 cells that ectopically express G12D KRas (FIG. 1B). The FY-A-100-2 was less potent, demonstrating the importance of lysine 85. Furthermore, FY-A-90-1A, which is identical to FY-A-100-1 except for having a "CH2" shorter side chain of residue 82 that forms the staple, was not active. FY-A-90-1B (non-stapled peptide of 1A) and FY-A-90-2A and 2B (stapled and non-stapled derivatives of FY-A-90-1A and 1B with alanine at position 85) also had little activity compared to DMSO control (FIG. 1B).

Disclosed herein are peptides having the following structure:

wherein X1 and X2 are amino acid residues bonded together (as shown by the dashed line). In one aspect, X1 is an aspartic acid residue (D). In another aspect, X1 is a glutamic acid residue (E). In one aspect, X2 is a lysine residue (K). In still another aspect X1 and X2 can be modified amino acid residues that form an alkyl, alkenyl, alkynyl, heteroaryl, aryl, ether, ester, thioether, thioester, amino, or amido containing bridge. That is, in this aspect, the disclosed peptides can have the following structure.

Wherein X3 is an alkyl, alkenyl, alkynyl, heteroaryl, aryl, ether, ester, thioether, thioester, amino, or amido moiety having from 5 to 25 atoms. Some additional examples of compounds are as follows:

FY-A-90-1A

Chemical Formula: $C_{76}H_{134}N_{26}O_{19}S_2$
Exact Mass: 1778.9760

FY-A-90-1B

Chemical Formula: $C_{76}H_{136}N_{26}O_{20}S_2$
Exact Mass: 1796.9866

-continued

FY-A-90-2A

Chemical Formula: $C_{73}H_{127}N_{25}O_{19}S_2$
Exact Mass: 1721.9181

FY-A-90-2B

Chemical Formula: $C_{73}H_{129}N_{25}O_{20}S_2$
Exact Mass: 1739.9287

FY-A-100-1

Chemical Formula: $C_{77}H_{136}N_{26}O_{19}S_2$
Exact Mass: 1792.99

FY-A-100-2

Chemical Formula: $C_{74}H_{129}N_{25}O_{19}S_2$
Exact Mass: 1735.93

-continued

FY-A-134-A

Chemical Formula: C₇₈H₁₄₂N₂₄O₁₉S
Exact Mass: 1751.0604
Molecular Weight: 1752.1765

FY-A-134-B

Chemical Formula: C₆₆H₁₁₇N₂₃O₁₆S₂
Exact Mass: 1551.85
Molecular Weight: 1552.93

FY-A-134-C-1

Chemical Formula: C₈₀H₁₄₁N₂₅O₁₈S₂
Exact Mass: 1804.03
Molecular Weight: 1805.28

FY-A-134-C-2

Chemical Formula: C₈₂H₁₄₅N₂₅O₁₈S₂
Exact Mass: 1832.0641
Molecular Weight: 1833.3154

FY-A-134-D-1

Chemical Formula: $C_{82}H_{145}N_{25}O_{18}S_2$
Exact Mass: 1832.0641
Molecular Weight: 1833.3154

FY-A-134-D-2

Chemical Formula: $C_{84}H_{149}N_{25}O_{18}S_2$
Exact Mass: 1860.0954
Molecular Weight: 1861.3686

The compositions disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compositions disclosed herein can be formulated such that an effective amount of the compound is combined with a suitable carrier in order to facilitate effective administration of the compound. The compositions used can also be in a variety of forms. These include, for example, solid, semisolid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Compositions suitable for use herein include, for example, aqueous sterile injection solutions, which can contain antioxidants, buffers, bacteriostats, and solutes that render the composition isotonic with the blood of the intended recipient; and aqueous and nonaqueous sterile suspensions, which can include suspending agents and thickening agents. The composition can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc.

Disclosed herein are methods of or preventing cancer in a subject, comprising administering to the subject an effective amount of a compound or composition as disclosed herein.

Also, disclosed herein are methods of killing a tumor cell that comprise contacting a tumor cell with an effective amount of a compound or composition as disclosed herein.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. Techniques for administering and formulating compounds for administration to a patient are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain.

The disclosed compositions can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a composition disclosed herein means introducing the composition into the system of the patient in need of treatment. In vivo application of the disclosed compositions can be accomplished by any suitable method and technique presently or prospectively known to those skilled in the art. For example, the disclosed compounds can be formulated in a physiologically-or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, and intraperitoneal administration, such as by injection. Administration of the disclosed compositions can be a single administration, or at continuous or distinct intervals as can be readily determined by a person skilled in the art.

The disclosed compositions can also be administered utilizing liposome technology, slow release capsules, implantable pumps, and biodegradable containers. These delivery methods can, advantageously, provide a uniform dosage over an extended period of time.

For the treatment of oncological disorders, the compositions disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein.

The disclosed compositions can be locally administered at one or more anatomical sites, such as sites of unwanted cell growth (such as a tumor site or benign skin growth, e.g., injected or topically applied to the tumor or skin growth). The disclosed compositions can be systemically administered, such as intravenously or orally, optionally in combination with a pharmaceutically acceptable carrier such as an inert diluent, or an assimilable edible carrier for oral delivery. They can be administered as hard or soft shell gelatin capsules or tablets, or incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compositions disclosed herein can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds disclosed herein can be applied in as a liquid or solid. However, it will generally be desirable to administer them topically to the skin as compositions, in combination with a dermatologically acceptable carrier, which can be a solid or a liquid. Compositions disclosed herein can be applied topically to a subject's skin to reduce the size (and can include complete removal) of malignant or benign growths, or to treat an infection site. Compositions disclosed herein can be applied directly to the growth in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition. Useful dosages of the compounds and compositions disclosed herein can be determined by comparing their in vitro activity, and in vivo activity in animal models. Methods for the extrapolation of effective dosages in mice, and other animals, to humans are known to the art.

Methods of Use

Further provided herein are methods of treating or preventing cancer in a subject, comprising administering to the subject an effective amount of a compound or composition as disclosed herein. Additionally, the method can further comprise administering an effective amount of ionizing radiation to the subject and/or another anti-cancer compound. Also disclosed are methods of imaging a cancer cell comprising contacting the cell with a compound as disclosed herein.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor. In a preferred aspect, the cancer is pancreatic cancer.

What is claimed is:

1. A compound having the following structure:

wherein X1 and X2 are amino acid residues bonded together.

2. The compound of claim 1, wherein X1 is an aspartic acid residue.

3. The compound of claim 1, wherein X1 is a glutamic acid residue.

4. The compound of claim 1, wherein X2 is a lysine residue.

5. The compound of claim 1, wherein X1 and X2 are modified amino acid residues that form an alkyl, alkenyl, alkynyl, heteroaryl, aryl, ether, ester, thioether, thioester, amino, or amido containing bridge.

6. The compound of claim 1, having the following structure wherein $X^3$ is an alkyl, alkenyl, alkynyl, heteroaryl, aryl, ether, ester, thioether, thioester, amino, or amido moiety having from 5 to 25 atoms.

7. A method for treating a tumor, comprising the step of administering to a patient in need thereof a therapeutically effective amount of a composition comprising the compound of claim 1.

8. The compound of claim 1, selected from one of the following compounds -continued

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: SYNTHETIC

<400> SEQUENCE: 1

Leu His Asp Cys Leu Met Lys Ala Leu Lys Val Arg Gly Leu Gln
1               5                   10                  15
```